(12) United States Patent
Gutierrez

(10) Patent No.: US 9,983,418 B2
(45) Date of Patent: May 29, 2018

(54) TACTILE INTERFACE FOR EYE-MOUNTABLE DEVICE

(71) Applicant: Verily Life Sciences LLC, Mountain View, CA (US)

(72) Inventor: Christian A. Gutierrez, San Jose, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days. days.

(21) Appl. No.: 15/228,766

(22) Filed: Aug. 4, 2016

(65) Prior Publication Data

US 2018/0039097 A1  Feb. 8, 2018

(51) Int. Cl.
*A61B 3/00* (2006.01)
*G02C 7/08* (2006.01)
*G02C 11/00* (2006.01)
*A61B 5/145* (2006.01)
*A61B 5/00* (2006.01)

(52) U.S. Cl.
CPC .......... *G02C 7/083* (2013.01); *A61B 5/14532* (2013.01); *A61B 5/6821* (2013.01); *A61B 5/6843* (2013.01); *A61B 5/746* (2013.01); *G02C 11/10* (2013.01)

(58) Field of Classification Search
CPC ..... G02C 7/083; G02C 11/10; A61B 5/14532; A61B 5/6821; A61B 5/6843; A61B 5/746
USPC .................................................... 351/159.03
See application file for complete search history.

(56) References Cited

U.S. PATENT DOCUMENTS

| 6,099,124 | A | * | 8/2000 | Hidaji | A61B 3/113 351/159.39 |
|---|---|---|---|---|---|
| 7,131,945 | B2 | | 11/2006 | Fink et al. | |
| 7,137,952 | B2 | | 11/2006 | Leonardi et al. | |
| 8,857,981 | B2 | * | 10/2014 | Pletcher | G02C 7/049 351/158 |
| 8,870,370 | B1 | | 10/2014 | Otis et al. | |

(Continued)

FOREIGN PATENT DOCUMENTS

| WO | 2012051167 A1 | 4/2012 |
|---|---|---|
| WO | 2016019346 A1 | 2/2016 |

OTHER PUBLICATIONS

Leonardi, M. et al., First Steps toward Noninvasive Intraocular Pressure Monitoring with a Sensing Contact Lens, Investigative Ophthalmology & Visual Science, Sep. 2004, 5 pages.

(Continued)

*Primary Examiner* — James Greece
(74) *Attorney, Agent, or Firm* — Christensen O'Connor Johnson Kindness PLLC

(57) ABSTRACT

An eye-mountable device includes an enclosure material shaped to be removably mounted over a cornea and to permit eyelid motion when the enclosure material is so mounted. The eye-mountable device also includes a tactile sensor system, including one or more pressure-sensitive sensors, disposed within the enclosure material and coupled to output a signal in response to pressure applied to the one or more pressure-sensitive sensors by a user. A controller is disposed within the enclosure material and electrically coupled to the tactile sensor system to receive the signal and, in response to the signal, control at least one other piece of circuitry in the eye-mountable device.

24 Claims, 9 Drawing Sheets

(56) References Cited

U.S. PATENT DOCUMENTS

| | | | |
|---|---|---|---|
| 8,909,311 B2* | 12/2014 | Ho | A61B 5/0004 |
| | | | 600/318 |
| 9,011,361 B2 | 4/2015 | de Juan, Jr. et al. | |
| 9,016,857 B2 | 4/2015 | Benko et al. | |
| 9,192,298 B2 | 11/2015 | Bouwstra et al. | |
| 9,778,492 B2 | 10/2017 | Pugh et al. | |
| 2012/0268712 A1* | 10/2012 | Egan | G02C 7/04 |
| | | | 351/159.34 |
| 2013/0261743 A1 | 10/2013 | Humphreys et al. | |
| 2014/0192312 A1 | 7/2014 | Pletcher et al. | |

OTHER PUBLICATIONS

Sensimed Triggerfish, Sensimed AG, 2013, 8 pages.
International Search Report and Written Opinion from the International Searching Authority, dated Oct. 18, 2017, or International Application No. PCT/US2017/044982, filed Aug. 1, 2017, 14 pages.

* cited by examiner

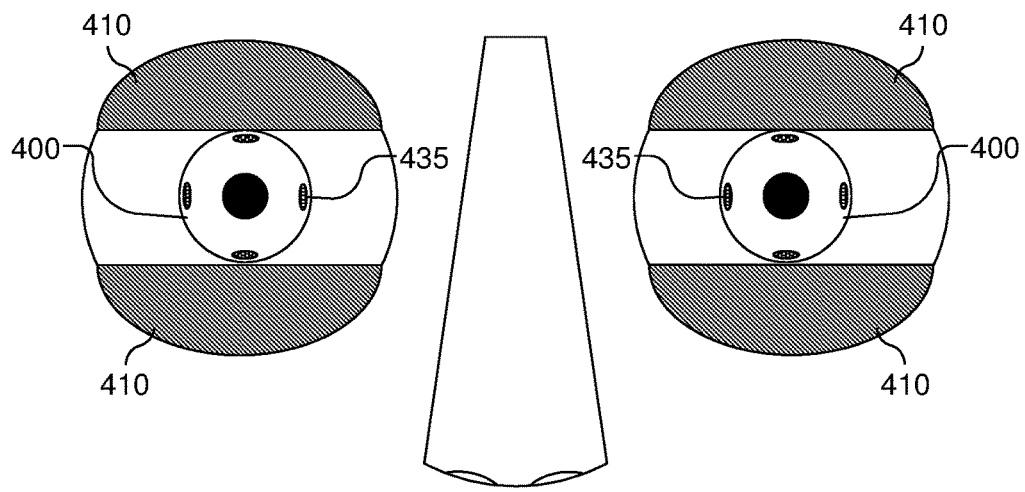
FIG. 4A
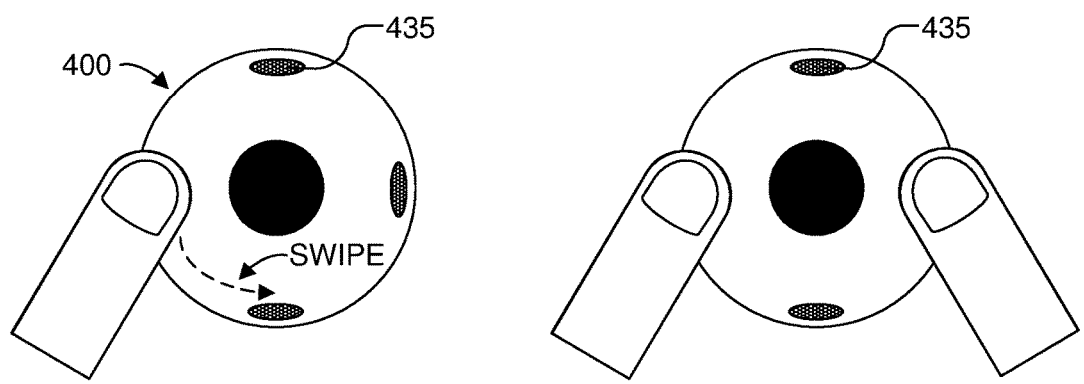
FIG. 4B    FIG. 4C
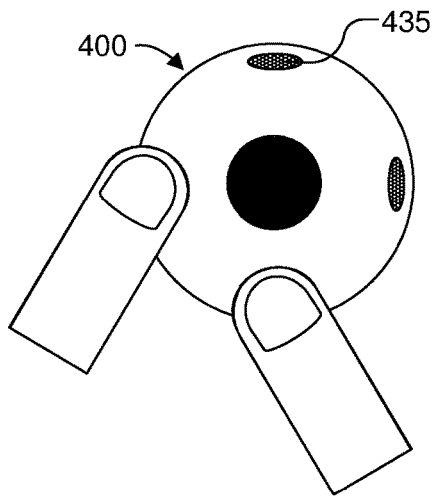    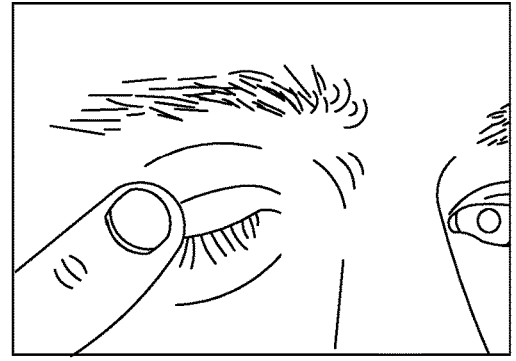
FIG. 4D    FIG. 4E

US 9,983,418 B2

1

TACTILE INTERFACE FOR EYE-MOUNTABLE DEVICE

TECHNICAL FIELD

This disclosure relates generally to the field of optics, and in particular but not exclusively, relates to contact lenses.

BACKGROUND INFORMATION

Accommodation is a process in which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of Presbyopia are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIG. 4A-4E illustrate use cases for the eye-mountable device of FIG. 1, in accordance with several embodiments of the disclosure.

DETAILED DESCRIPTION

Embodiments of an apparatus and method for a tactile interface for an eye-mountable device are described herein. In the following description numerous specific details are set forth to provide a thorough understanding of the embodiments. One skilled in the relevant art will recognize; however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein is an eye-mountable device (or smart contact lens) that includes a tactile sensor system for manual communication with the eye-mountable device. As will be shown, placing a tactile sensor system in a contact lens may be useful for a variety of reasons, including providing a method of direct communication between the user of the smart contact lens and the lens itself. Simply by touching the smart contact lens, the user may send instructions to the lens. Direct communication may be desirable when the lens requires immediate user input, when the lens is malfunctioning, or when the user wants to turn the lens on/off. However, one skilled in the art will appreciate that there are many situations in which direct user communication with a smart contact lens is useful.

Figure 1:
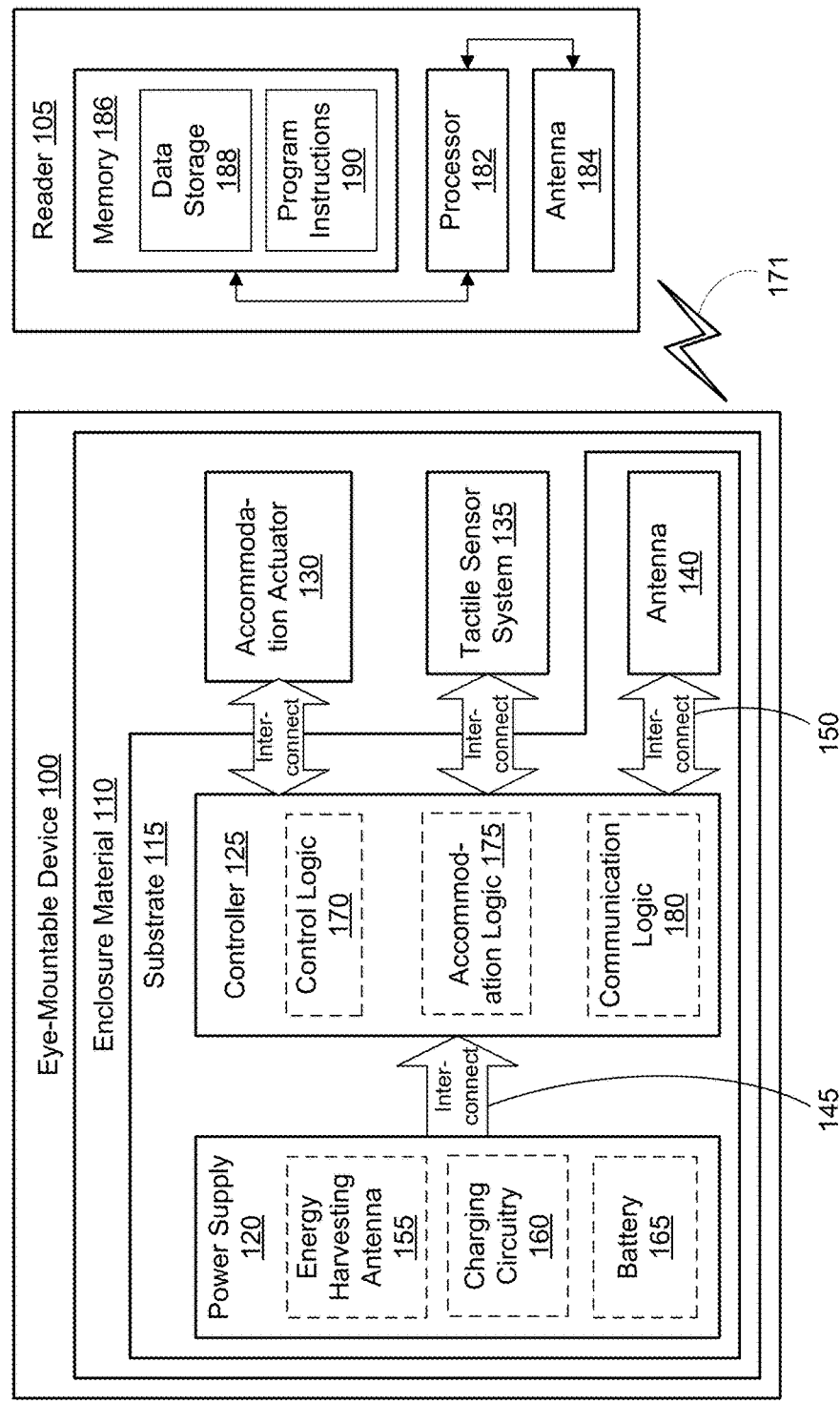
FIG. 1 is a functional block diagram of an eye-mountable device with a tactile sensor system, in accordance with an embodiment of the disclosure.

FIG. 1 is a functional block diagram of eye-mountable device 100 with a tactile sensor system 135, in accordance with an embodiment of the disclosure. In the depicted embodiment, eye-mountable device 100 includes an enclosure material 110 formed to be contact-mounted to a corneal surface of an eye. A substrate 115 is embedded within or surrounded by enclosure material 110 to provide a mounting surface for a power supply 120, a controller 125, an antenna 140, and various interconnects 145 and 150. The illustrated embodiment of power supply 120 includes an energy harvesting antenna 155, charging circuitry 160, and a battery 165. The illustrated embodiment of controller 125 includes control logic 170, accommodation logic 175, and communication logic 180. As shown, accommodation actuator 130 and tactile sensor system 135 are disposed in the enclosure material 110. Because eye-mountable device 100 includes electronics and is configured to be contact-mounted to an eye, it is also referred to herein as a contact lens, smart contact lens, or electronic contact lens.

Enclosure material 110 in eye-mountable device 100 is configured to be removeably mounted over a cornea of a user's eye, and has a size and shape that permits eyelid motion when enclosure material 110 is mounted. Tactile sensor system 135 may include one or more pressure-sensitive sensors and be disposed within the enclosure material 110. Tactile sensor system 135 is coupled to output a signal in response to pressure applied to the one or more pressure-sensitive sensors by a user. Controller 125 is disposed within enclosure material 110 and electrically coupled to tactile sensor system 135 to receive the signal and, in response to the signal, control at least one other piece of circuitry (e.g., accommodation actuator 130, antenna 140, power supply 120, or other pieces of circuitry not depicted such as a glucose sensor) in eye-mountable device 100.

Power supply 120 supplies operating voltages to the controller 125 and/or the accommodation actuator 130. Antenna 140 is operated by the controller 125 to communicate information to and/or from eye-mountable device 100. In the illustrated embodiment, antenna 140, controller 125, and power supply 120 are disposed on/in substrate 115, while tactile sensor system 135 and accommodation actuator 130 are disposed in enclosure material 110 (not in/on substrate 115). However, in other embodiments, the various pieces of circuitry and devices contained in eye-mountable device 100 may be disposed in/on substrate 115 or in enclosure material 110, depending on the specific design of eye-mountable device 100. For example, in one embodiment, accommodation actuator 130 may be disposed on a transparent substrate.

Substrate 115 includes one or more surfaces suitable for mounting controller 125, power supply 120, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. A combination of resists, masks, and deposition techniques can be employed to pattern materials on substrate 115. Substrate 115 can be a relatively rigid material, such as polyethylene terephthalate ("PET") or another material sufficient to structurally support the circuitry and/or electronics within enclosure material 110. Eye-mountable device 100 can alternatively be arranged with a group of unconnected substrates rather than a single substrate 115. For example, controller 125 and power supply 120 can be mounted to one substrate 115, while antenna 140 is mounted to another substrate 115 and the two can be electrically connected via interconnects. Substrate 115 may also be a continuous piece of semiconductor, housing all or some of the aforementioned pieces of device architecture as integrated circuitry.

Substrate 115 can be shaped as a flattened ring with a radial width dimension sufficient to provide a mounting platform for the embedded electronic components. Substrate 115 can have a thickness sufficiently small to allow substrate 115 to be embedded in enclosure material 110 without adversely influencing the profile of eye-mountable device 100. Substrate 115 can have a thickness sufficiently large to provide structural stability suitable for supporting the electronics mounted thereon. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In the illustrated embodiment, power supply 120 includes a battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Additionally or alternatively, power supply 120 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for receiving signals from sensors monitoring the orientation of the eye, determining the current gaze direction or focal distance of the user, and manipulating accommodation actuator 130 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides back-scatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

The illustrated embodiment also includes reader 105 with a processor 182, an antenna 184, and memory 186. Memory 186 in reader 105 includes data storage 188 and program instructions 190. As shown reader 105 may be disposed outside of eye-mountable device 100, but may be placed in its proximity to charge eye-mountable device 100, send instructions to eye-mountable device 100, and/or extract data from eye-mountable device 100. In one embodiment, reader 105 may resemble a conventional contact lens holder that the user places eye-mountable device 100 in at night to charge, extract data, clean the lens, etc.

External reader 105 includes an antenna 184 (or group of more than one antennae) to send and receive wireless signals 171 to and from eye-mountable device 100. External reader 105 also includes a computing system with a processor 182 in communication with a memory 186. Memory 186 is a non-transitory computer-readable medium that can include, without limitation, magnetic disks, optical disks, organic memory, and/or any other volatile (e.g., RAM) or non-volatile (e.g., ROM) storage system readable by the processor 182. Memory 186 can include a data storage 188 to store indications of data, such as data logs (e.g., user logs), program settings (e.g., to adjust behavior of eye-mountable device 100 and/or external reader 105), etc. Memory 186 can also include program instructions 190 for execution by processor 182 to cause the external reader 105 to perform processes specified by the instructions 190. For example, program instructions 190 can cause external reader 105 to provide a user interface that allows for retrieving information communicated from eye-mountable device 100 or allows transmitting information to eye-mountable device 100 to program or otherwise select operational modes of eye-mountable device 100. External reader 105 can also include one or more hardware components for operating antenna 184 to send and receive wireless signals 171 to and from eye-mountable device 100.

External reader 105 can be a smart phone, digital assistant, or other portable computing device with wireless connectivity sufficient to provide the wireless communication link 171. External reader 105 can also be implemented as an antenna module that can be plugged in to a portable computing device, such as in an embodiment where the communication link 171 operates at carrier frequencies not commonly employed in portable computing devices. In some instances, external reader 105 is a special-purpose device configured to be worn relatively near a wearer's eye to allow the wireless communication link 171 to operate with a low power budget. For example, the external reader 105 can be integrated in a piece of jewelry such as a necklace, earring, etc. or integrated in an article of clothing worn near the head, such as a hat, headband, etc.

Figure 2A:
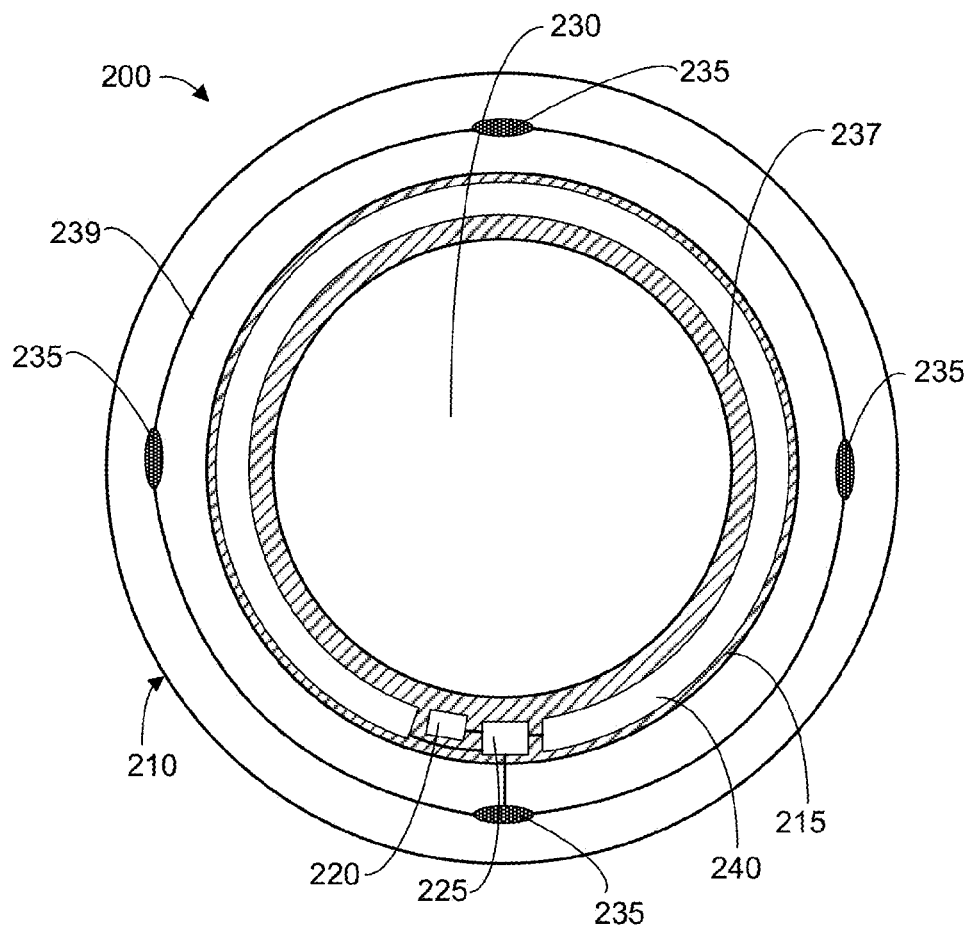
FIG. 2A is a top view of the eye-mountable device of FIG. 1, in accordance with an embodiment of the disclosure.

FIG. 2A is a top view of eye-mountable device 200 (which is an embodiment of the eye-mountable device 100 of FIG. 1). The illustrated embodiment of eye-mountable device 200 includes an enclosure material 210, a substrate 215, a power supply 220, a controller 225, an accommodation actuator 230, a tactile sensor system (including individual pressure-sensitive sensors 235), and an antenna 240. It should be appreciated that FIGS. 2A and 2B are not necessarily drawn to scale, but have been illustrated for purposes of explanation only in describing the arrangement of the example eye-mountable device 200.

Eye-mountable device 200 is a circular contact lens with a tactile sensor system, including one or more pressure-sensitive sensors 235. One or more pressure-sensitive sensors 235 are disposed within the contact lens, and coupled to output a signal in response to pressure applied to the one or more pressure-sensitive sensors 235 by a user. The one or more pressure-sensitive sensors 235 are disposed around a periphery of eye-mountable device 200 (and around the accommodation actuator 230) such that light entering an eye of the user is unobstructed by the one or more pressure-sensitive sensors 235 (when enclosure material 210 is mounted over the cornea). Accommodation actuator 230 is also disposed in the contact lens to optically align with a cornea of the user when the contact lens is mounted in an eye of the user. Controller 225 is disposed in the contact lens and electrically coupled to the tactile sensor system and the accommodation actuator 230. Controller 225 includes logic that when executed by controller 225 causes controller 225 to perform operations including: (1) controlling one or more other pieces of circuitry disposed in the contact lens in response to a signal from the tactile sensor system; and (2) electrically manipulating accommodation actuator 230 to automatically change an optical power of the contact lens in response to a state of the eye as measured by the contact lens. In one embodiment, controller 225 may manipulate accommodation actuator 230 in response to the pressure applied by the user to the one or more pressure-sensitive sensors 235.

In the depicted embodiment, interconnects 239 extend between one or more pressure-sensitive sensors 235 and may include many small wires to individually transmit signals from one or more pressure-sensitive sensors 235 to controller 225. Power supply 220 is also coupled to controller 225, accommodation actuator 230, and antenna 240 to supply power to controller 225, supply power to accommodation actuator 230, and/or receive power from antenna 240.

Figure 2B:
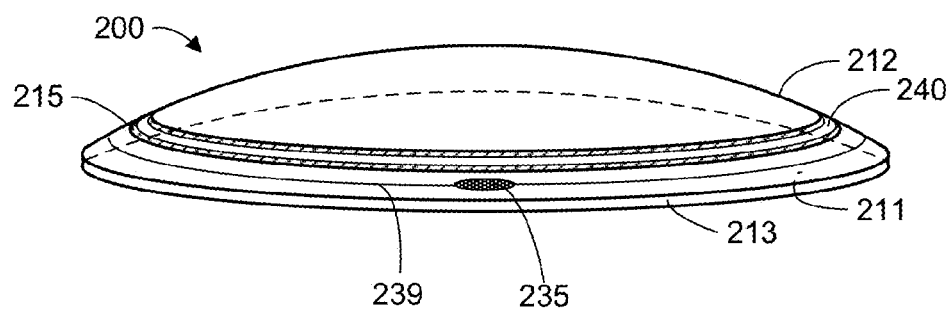
FIG. 2B is a perspective view of the eye-mountable device of FIG. 2A, in accordance with an embodiment of the disclosure.

FIG. 2B is a perspective view of eye-mountable device 200 of FIG. 2A, in accordance with an embodiment of the disclosure. Enclosure material 210 of eye-mountable device 200 is shaped as a curved disk. As shown, to facilitate contact-mounting, the enclosure material 210 can have a concave surface configured to adhere ("mount") to a moistened corneal surface (e.g., by capillary forces with a tear film coating the corneal surface). Additionally, the eye-mountable device 200 may be adhered by a vacuum force between the corneal surface and enclosure material 210 due to the concave curvature. While mounted with the concave surface against the eye, the outward-facing surface of the enclosure material 210 can have a convex curvature that is formed to not interfere with eye-lid motion while the eye-mountable device 200 is mounted to the eye.

Enclosure material 210 may be a substantially transparent material to allow incident light to be transmitted to the eye while eye-mountable device 200 is mounted to the eye. Enclosure material 210 may be a biocompatible material similar to those employed to form vision correction and/or cosmetic contact lenses in optometry, such as a polymeric material like polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise.

FIGS. 3A-3E illustrate configurations of pressure-sensitive sensors 335 disposed on eye-mountable device 300, in accordance with several embodiments of the disclosure. It should be noted that other pieces of device architecture are present but not depicted to avoid obscuring certain aspects of the disclosure. Further accommodation actuator 330 is depicted in the center of the device for a frame of reference, but in other embodiments, accommodation actuator 330 may not be present.

As shown, pressure-sensitive sensors 335 may be mounted/disposed around a periphery of eye-mountable device 300 such that light entering an eye of the user is unobstructed by one or more pressure-sensitive sensors 335 when the enclosure material is mounted over the cornea. Although in the depicted embodiment pressure-sensitive sensors 335 are free-floating in the bulk of eye-mountable device 300, in other embodiments, they may be connected to a substrate. Furthermore, pressure-sensitive sensors 335 are disposed in the annular region of eye-mountable device 300 (defined by the outer edge of eye-mountable device 300 and the pupil radius). However, in other embodiments pressure-sensitive sensors 335—when composed of optically transparent material—may be disposed over the pupil without obstructing vision.

Figure 3A:
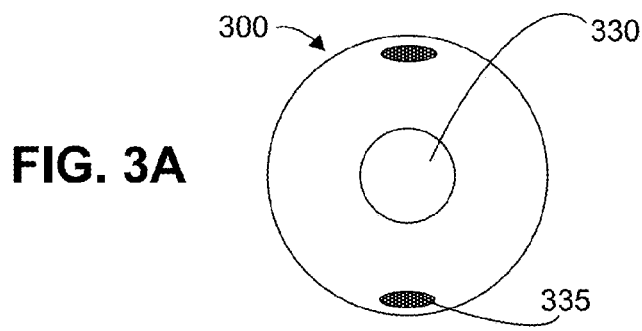
FIGS. 3A-3E illustrate configurations of pressure-sensitive sensors, in accordance with several embodiments of the disclosure.

FIG. 3A shows two pressure-sensitive sensors 335 disposed on opposite sides of eye-mountable device 300. Accordingly, FIG. 3A has an even number of pressure-sensitive sensors 335 spaced evenly around the periphery of eye-mountable device 300.

Figure 3B:
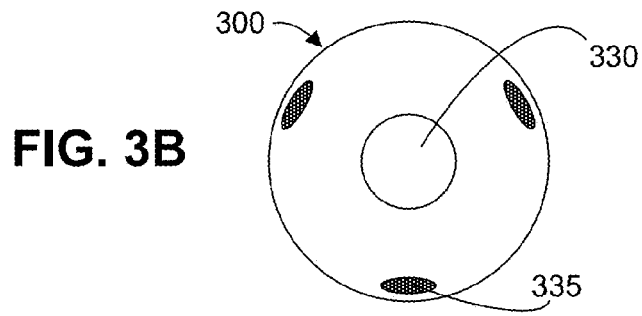

FIG. 3B shows three pressure-sensitive sensors 335 disposed around eye-mountable device 300. In other words, FIG. 3B has an odd number of pressure-sensitive sensors 335 spaced evenly around the periphery of eye-mountable device 300.

Figure 3C:
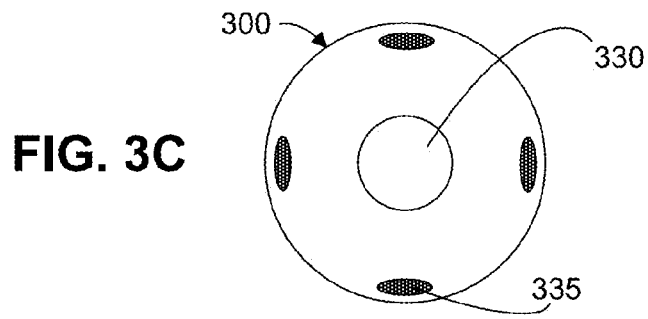

FIG. 3C shows four pressure-sensitive sensors 335 disposed on opposite sides of eye-mountable device 300. Accordingly, FIG. 3C has an even number of pressure-sensitive sensors 335 spaced evenly around the periphery of eye-mountable device 300.

Figure 3D:
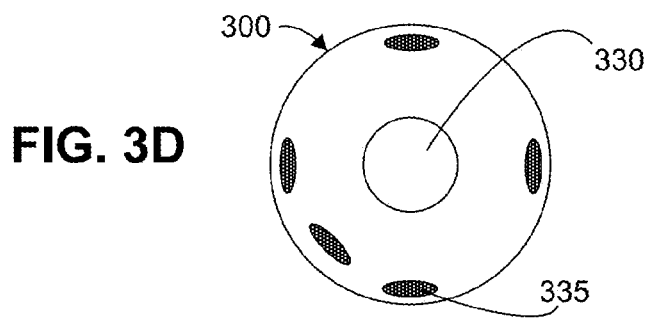

FIG. 3D shows five pressure-sensitive sensors 335 disposed around eye-mountable device 300. As shown, FIG. 3D has an odd number of pressure-sensitive sensors 335 spaced at varying intervals around the periphery of eye-mountable device 300. In some situations, non-symmetrical sensor configurations may be advantageous to detect the specific location/orientation of user-applied pressure on the lens.

Figure 3E:
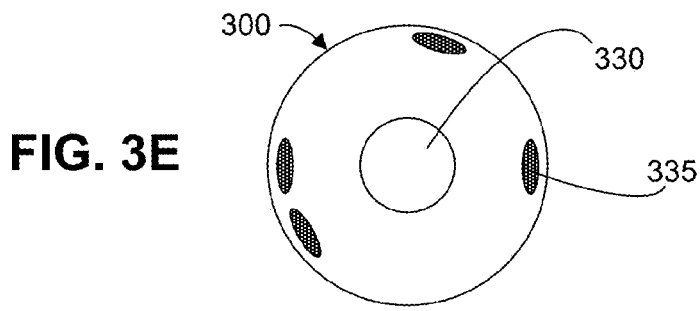

Similarly, FIG. 3E shows four pressure-sensitive sensors 335 disposed around eye-mountable device 300. The pressure-sensitive sensors 335 are disposed unevenly around the periphery of the device.

Although FIGS. 3A-3E show configurations of pressure-sensitive sensors 335 with 2, 3, 4, and 5 pressure-sensitive sensors 335 disposed in the device, one skilled in the art will appreciate that other configurations may have any number of pressure-sensitive sensors 335 disposed in any configuration on eye-mountable device 300. Different configurations may be advantageous in different eye-mountable device 300 use cases (e.g., a device that has various sensor systems for monitoring body chemistry may warrant a different tactile sensor system than a device for active accommodation).

FIG. 4A-4E illustrate use cases for the eye-mountable device of FIG. 1, in accordance with several embodiments of the disclosure.

FIG. 4A depicts eye-mountable device 400 disposed in the eyes of a user, and optically aligned with the iris so light may enter the user's eyes. As shown both eyes contain an eye-mountable device 400. However, in other embodiments only one eye may contain the eye-mountable device 400. As stated above, eye-mountable device 400 is configured to not interfere with blinking by the user. While eye-mountable device 400 is mounted to the user's cornea, the user should be able to blink naturally without eye-mountable device 400 becoming dislodged or causing discomfort.

FIG. 4B depicts several motions that may be used to control eye-mountable device 400 via the tactile interface. Eye-mountable device 400 may be configured to receive user input by the user pressing with their finger(s) on the one or more pressure-sensitive sensors 435. In the depicted embodiment, pressing includes using a single finger to press on a single pressure-sensitive sensor 335. FIG. 4B also depicts an optional swiping motion across the surface of the device to contact one or more of pressure-sensitive sensors 435. While the depicted embodiment shows a relatively simple swiping motion, other more complex swiping motions may be employed such as a swipe circumnavigating the periphery of the eye-mountable device 400, or the like.

FIG. 4C depicts another motion that may be used to control eye-mountable device 400. As shown the user may use two figures to press on eye-mountable device 400. This may provide a different signal or sub-signal to eye-mountable device 400 than the motion in FIG. 4B. For instance, the swipe motion in FIG. 4A may turn the device on and off, while the two-finger press motion in FIG. 4B may be a manual override signal for a piece of circuitry in the device.

FIG. 4D depicts yet another possible motion to control eye-mountable device 400. Unlike FIG. 4C (where two fingers press on opposite sides of the device), FIG. 4D shows two fingers press on sensors 435 adjacent to one another. Once again, this configuration of pressures on the surface of eye-mountable device 400 may send yet another signal to the device.

FIG. 4E illustrates that the one or more pressure-sensitive sensors 435 may be configured to receive pressure from the user through an eyelid of the user. While the motions depicted in FIGS. 4B-4D were illustrated as occurring on the lens itself (to show the location of the user's finger relative to the one or more pressure-sensitive sensors 435) all of these motions, and other motions not depicted, may be received by eye-mountable device 400 through the eyelids of the user. Receiving the pressure through the eyelid may enhance user comfort while operating eye-mountable device 400. Further, one skilled in the art will appreciate that the types of motions disclosed here should not be deemed limiting; eye-mountable device 400 may be configured to receive any number of different signals from the user, and pressure-sensitive sensors 435 may be oriented in any number of ways to enhance the signal or elicit information about the signal (e.g., one or two finger press, direction of swipe, tap, multiple tap, touch and hold, etc.). The signals received from the user may correspond to any action in the lens including: manual override, power save mode, accommodation mode, zoom in/out, switching speed increase/decrease, off/disable/restart of lens, change color of lens, etc.

Figure 5:
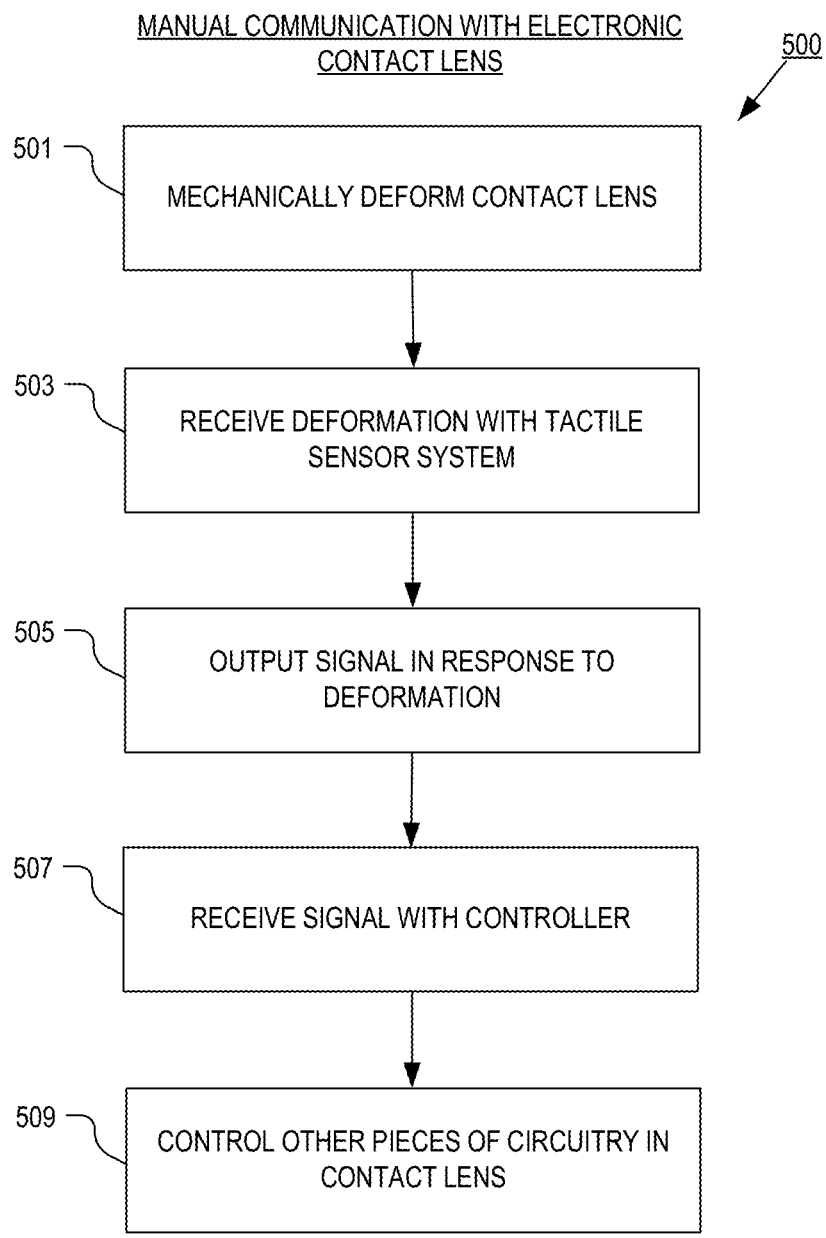
FIG. 5 is a flow chart illustrating a method for manual communication with an electronic contact lens, in accordance with an embodiment of the disclosure.

FIG. 5 is a flow chart illustrating a method 500 for manual communication with an electronic contact lens, in accordance with an embodiment of the disclosure. The order in which some or all of the method blocks appear should not be deemed limiting. Rather, one of ordinary skill in the art having the benefit of the present disclosure will understand that some of the method blocks may be executed in a variety of orders not illustrated, or even in parallel. Additionally, blocks may be added to, or excluded from, method 500, in accordance with embodiments of the disclosure.

Block 501 illustrates mechanically deforming a portion of the electronic contact lens. In one embodiment, mechanically deforming includes pressing on one or more pressure-sensitive sensors through an eyelid of a user. In one embodiment, the user may mechanically deform a portion of the electronic contact lens in response to a communication signal from the electronic contact lens to the user. For example, a diode in the contact lens may flash in response to the user's glucose being too high or too low. The user may acknowledge this signal by pressing on the lens.

Block 503 shows receiving the mechanical deformation with a tactile sensor system disposed in the electronic contact lens. The tactile sensor system includes one or more pressure-sensitive sensors disposed proximate to a periphery of the electronic contact lens. In one embodiment, the location of the deformation corresponds to a plurality of sub-signals to control the contact lens. For example, a user may press on the contact lens with one finger, press with two fingers, or a make a swiping motion across the lens. Each one of these actions may correspond to a different sub-signal received by the contact lens. For instance, a first sub-signal may be an override signal for one or more pieces of circuitry in the electronic contact lens, a second sub-signal may be an on/off signal, and a third sub-signal may be an adjustment signal to adjust an optical power of an accommodation actuator disposed in the electronic contact lens.

Block 505 includes outputting a signal from the tactile sensor system in response to the mechanical deformation of the electronic contact lens. In one embodiment the signal may be an analog signal proportional to the amount of contact lens deformation. In another embodiment, the signal may be a digital signal that is output in response to a threshold amount of deformation in the contact lens.

Block 507 shows receiving the signal with a controller coupled to the tactile sensor system, where the controller is coupled to one or more other pieces of circuitry in the electronic contact lens.

Block 509 depicts the contact lens controlling other pieces of circuitry in the contact lens. In embodiments where the electronic contact lens includes an accommodation actuator, the accommodation actuator may adjust to a certain focal distance in repose to the pressure-originated signal. For example, the accommodation actuator may be programmed to have one or more preset modes for viewing things up-close (e.g., reading) or far way (e.g., bird watching). Pressing on the contact lens in a particular way (e.g., with one finger, two fingers, etc.) may send a signal to the accommodation actuator to adjust to one of these preset settings.

Figure 6A:
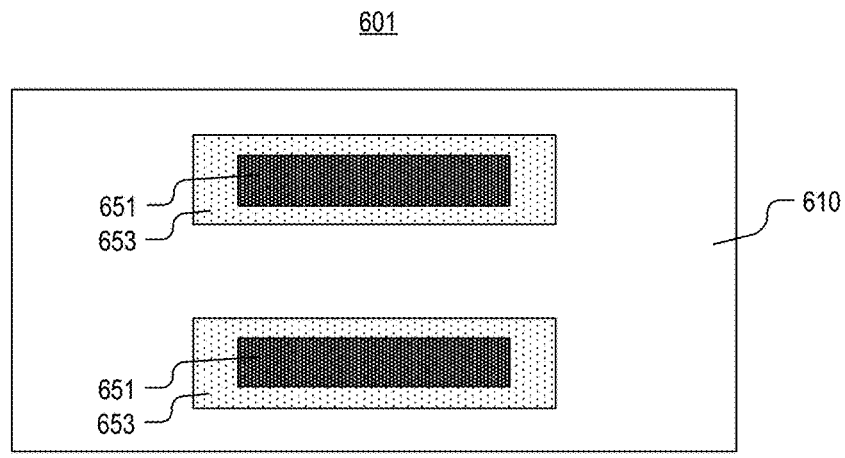
FIGS. 6A-6B illustrate a capacitive sensor for use in the eye-mountable device of FIG. 1, in accordance with several embodiments of the disclosure.
Figure 6B:
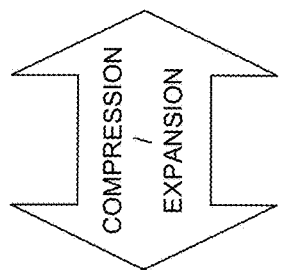
Figure 6B:
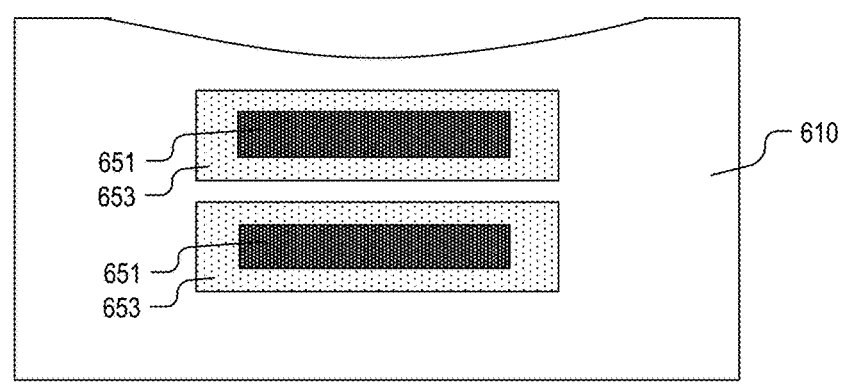

FIGS. 6A-6B illustrate capacitive sensor 601 for use in the eye-mountable device of FIG. 1, in accordance with embodiments of the disclosure. In the depicted embodiment, capacitive sensor 601 includes two vertically oriented field plates 651 disposed in enclosure material 610. Field plates 651 are separated from each other by a distance. The two field plates 651 are coated with coating material 653. Coating material 653 may be resistive and help prevent short circuiting field plates 651 and/or other pieces of circuitry.

As shown in FIG. 6B, when pressure is applied to enclosure material 610, the field plates 651 move closer together. The distance between the field plates 651 alters the capacitance measurements between them. Accordingly, this capacitance measurement may be output to the controller in the eye-mountable device. Either an analog or digital signal may be output to the controller; informing the controller that pressure has been applied to the eye-mountable device. Field plates 651 may be coupled to the controller by wires running through the eye-mountable device. Furthermore, bumps on enclosure material 610 (proximate to field plates 651) may provide for enhanced deformation and greater signal strength by increasing localized deformations.

Figure 7A:
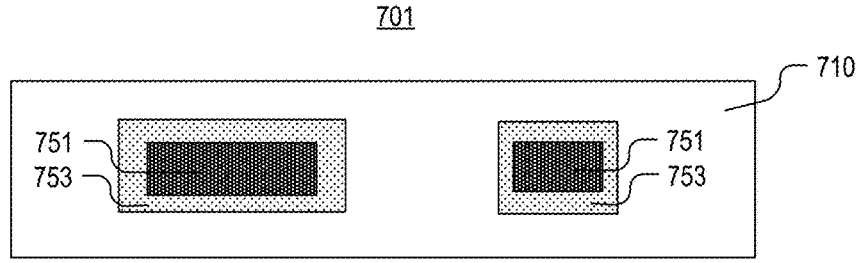
FIGS. 7A-7B illustrate a capacitive sensor for use in the eye-mountable device of FIG. 1, in accordance with several embodiments of the disclosure.
Figure 7B:
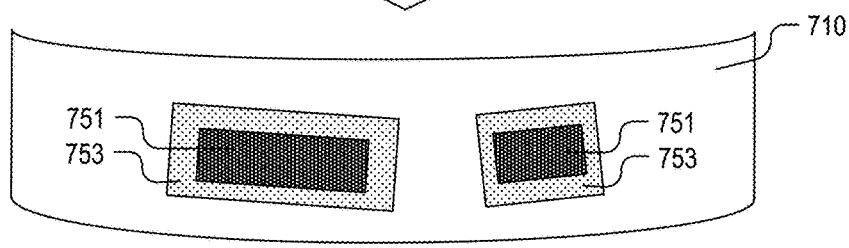

FIGS. 7A-7B illustrate capacitive sensor 701 for use in the eye-mountable device of FIG. 1, in accordance with embodiments of the disclosure. In the depicted embodiment, capacitive sensor 701 includes two horizontally oriented field plates 751 disposed in enclosure material 710. Field plates 751 are separated from each other by a lateral distance. The two field plates 751 are coated with coating material 753. Coating material 753 may be resistive and help prevent short circuiting the plates 751 and/or other pieces of circuitry. In the illustrated embodiment one field plate 751 is smaller than the other field plate 751. This may be due to space limitations inside the contact lens, or to optimize the electric field strength between the two field plates. In one embodiment, field plates 751 may either be metal traces running through the lens, or may be discrete solid chips each forming a ridged conducting island.

As shown in FIG. 7B, when pressure is applied to enclosure material 710, field plates 751 move and rotate with respect to their previous orientation. The changing distance between field plates 751 and their orientation, alters the capacitance measurements between field plates 751. Accordingly, capacitance measurement may be output to the controller in the eye-mountable device.

One skilled in the art will appreciate that capacitive sensor systems 601 and 701 depicted in FIGS. 6A-6B and FIGS. 7A-7B are merely illustrations of two possible capacitive sensor systems. Other geometries/structures may be employed, in accordance with the teachings of the present disclosure.

Figure 8A:
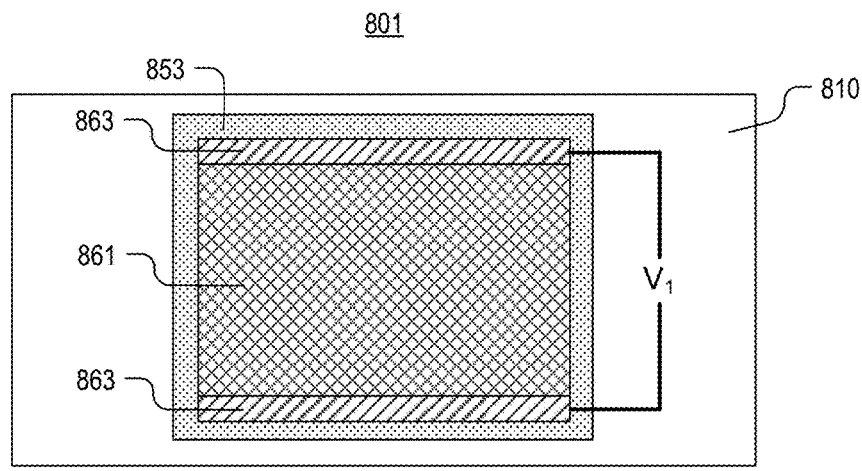
FIGS. 8A-8B illustrate a piezoelectric sensor for use in the eye-mountable device of FIG. 1, in accordance with several embodiments of the disclosure.
Figure 8B:
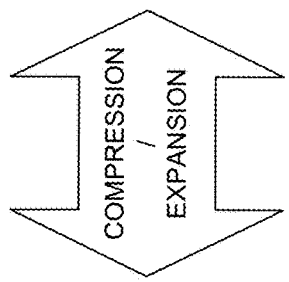
Figure 8B:
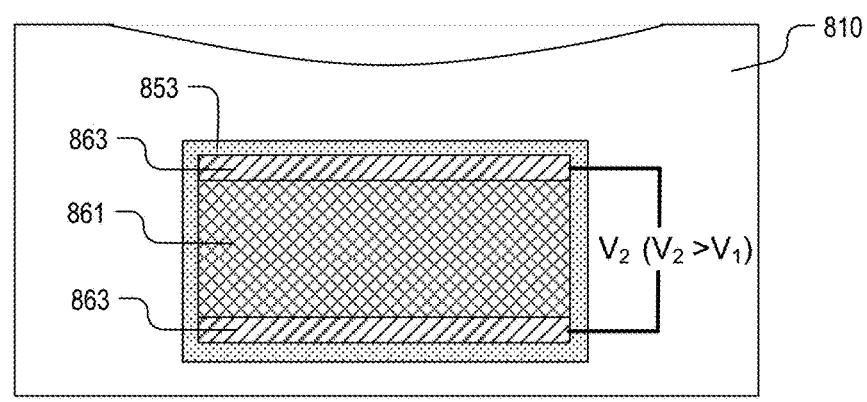

FIGS. 8A-8B illustrate piezoelectric sensor 801 for use in the eye-mountable device of FIG. 1, in accordance with embodiments of the disclosure. As depicted, piezo electric material 861 is disposed between two electrodes 863. Piezo electric material 861 and electrodes 863 are disposed in coating material 853. Piezoelectric sensor 801 is disposed in enclosure material 810 of the eye-mountable device.

As shown in FIG. 8B when pressure is applied to the eye mounted device, piezoelectric material 861 compresses and produces an external voltage ($V_2$) proportional to the pressure applied to the device. This voltage may be used to determine the presence of user contact (as a binary signal) or may be used to determine the presence and magnitude of user contact (as an analog signal).

One skilled in the art will appreciate that piezoelectric sensor system 801 depicted in FIGS. 8A-8B is merely an illustration of one possible piezoelectric sensor system. Other geometries/structures may be employed, in accordance with the teachings of the present disclosure. Further a wide variety of materials may employed to make piezoelectric sensor system 801 including piezoelectric polymers, biological materials, oxides, or the like.

Figure 9A:
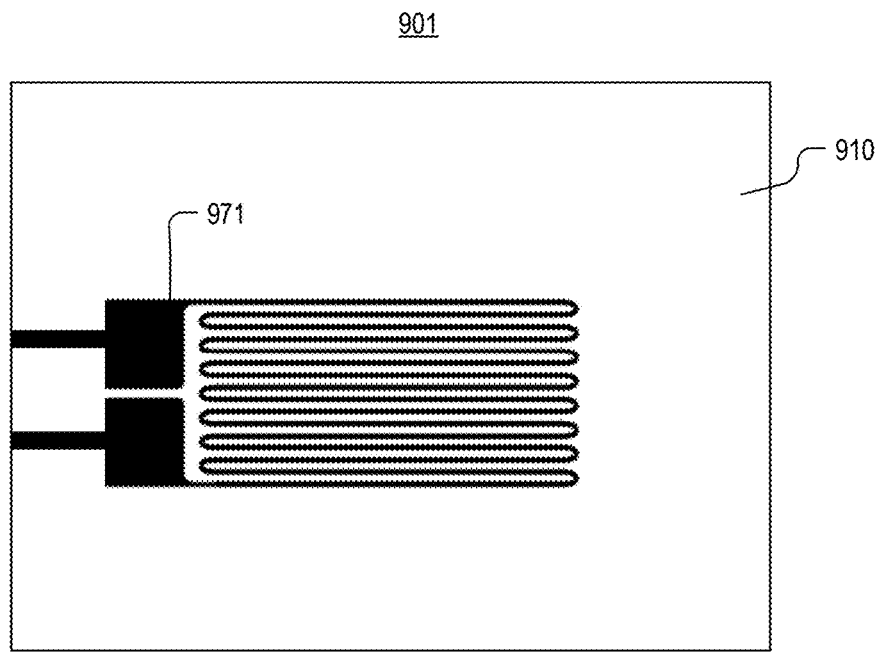
FIGS. 9A-9B illustrate a piezoresistive sensor for use in the eye-mountable device of FIG. 1, in accordance with several embodiments of the disclosure.
Figure 9B:
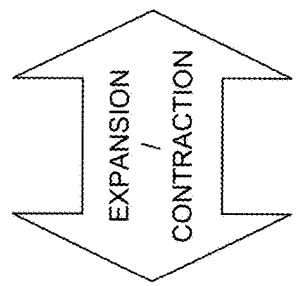
Figure 9B:
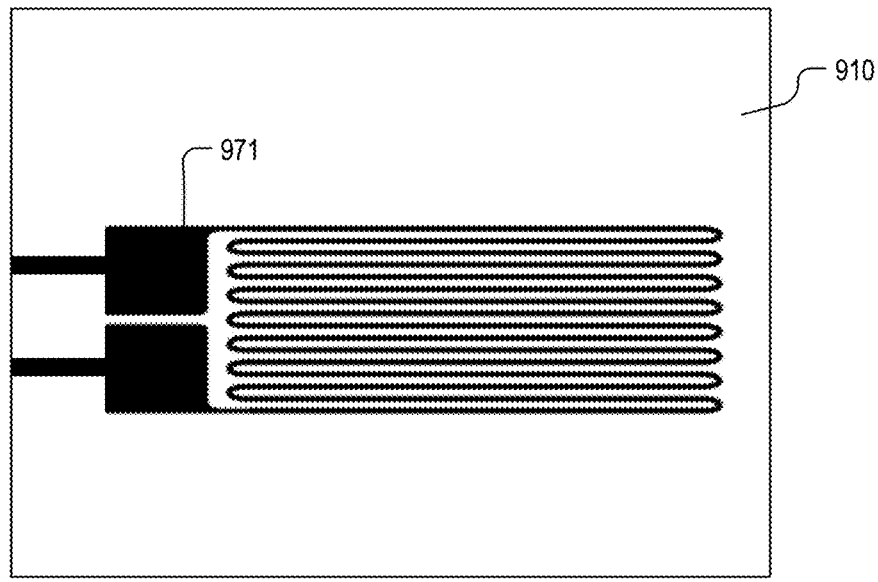

FIGS. 9A-9B illustrate a piezoresistive sensor system 901 for use in the eye-mountable device of FIG. 1, in accordance with embodiments of the disclosure. In the depicted embodiment, the piezoresistive sensor system 901 includes a strain gauge 971 disposed in enclosure material 910 of the eye-mountable device. As depicted in FIG. 9B, when pressure is applied to the eye-mountable device, enclosure material 910 may laterally expand, as a result, the resistance of strain gauge 971 may increase. Strain gauge 971 may be oriented horizontally with respect to surface normal of the eye-mountable device, may be oriented vertically with respect to surface normal of the eye-mountable device, or may be oriented at any angle in-between. Strain gauge 971 may take any orientation within the eye-mountable device, as different orientations may improve responsiveness of the strain gauge 971.

Further, one skilled in the art may appreciate that while the embodiment depicted in FIGS. 9A-9B illustrates a simple strain gauge, other strain/stress sensors may be used to detect pressure. Other geometries/structures/piezoresistive devices may be employed, in accordance with the teachings of the present disclosure.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-mountable device, comprising:
   an enclosure material shaped to be removably mounted over a cornea and to permit eyelid motion when the enclosure material is so mounted;
   an accommodation actuator coupled to change an optical power of the eye-mountable device;
   a tactile sensor system, including one or more pressure-sensitive sensors, disposed within the enclosure material and coupled to output a signal in response to pressure applied by a user to the one or more pressure-sensitive sensors; and
   a controller disposed within the enclosure material and electrically coupled to the tactile sensor system to receive the signal, wherein the controller includes logic that when executed by the controller causes the eye-mountable device to perform operations including:
   determining that the pressure applied is from a finger of a user through an eyelid of the user; and
   electrically manipulating the accommodation actuator to change an optical power of the contact lens in response to the signal from the tactile sensor system, which is generated in response to pressure applied to the one or more pressure-sensitive sensors by the finger of the user.

2. The eye-mountable device of claim 1, wherein the eye-mountable device is circular and the one or more pressure-sensitive sensors are disposed around a periphery of the eye-mountable device such that light entering an eye of the user is substantially unobstructed by the one or more pressure-sensitive sensors when the enclosure material is mounted over the cornea.

3. The eye-mountable device of claim 2, wherein the one or more pressure-sensitive sensors include an even number of pressure-sensitive sensors spaced evenly around the periphery of the eye-mountable device.

4. The eye-mountable device of claim 2, wherein the one or more pressure-sensitive sensors include an odd number of pressure-sensitive sensors spaced evenly around the periphery of the eye-mountable device.

5. The eye-mountable device of claim 2, wherein the one or more pressure-sensitive sensors are unevenly spaced around the periphery of the eye-mountable device.

6. The eye-mountable device of claim 1, wherein the one or more pressure-sensitive sensors include at least one of a piezoresistive sensor, or a piezoelectric sensor.

7. A contact lens, comprising:
   a tactile sensor system, including one or more pressure-sensitive sensors, disposed within the contact lens and coupled to output a signal in response to pressure applied to the one or more pressure-sensitive sensors by a finger of a user, through an eyelid of the user, when the contact lens is mounted in the eye of the user;
   an accommodation actuator disposed in the contact lens to optically align with a cornea of the user when the contact lens is mounted on an eye of the user; and
   a controller disposed in the contact lens and electrically coupled to the tactile sensor system and the accommodation actuator, wherein the controller includes logic that when executed by the controller causes the contact lens to perform operations including:
   controlling one or more other pieces of circuitry disposed in the contact lens in response to the signal from the tactile sensor system; and
   electrically manipulating the accommodation actuator to change an optical power of the contact lens in response to the signal from the tactile sensor system, which is generated in response to pressure applied to the one or more pressure-sensitive sensors by the finger of the user.

8. The contact lens of claim 7, wherein controlling the one or more other pieces of circuitry includes manipulating the accommodation actuator in response to the pressure applied by the user.

9. The contact lens of claim 7, wherein controlling the one or more other pieces of circuitry includes turning the contact lens on and off.

10. The contact lens of claim 7, further comprising:
    a substrate having a ring shape disposed within the contact lens, wherein the controller is disposed on the substrate, and wherein the ring shape of the substrate encircles the accommodation actuator;
    a battery disposed on the substrate to power the controller, the tactile sensor system, and the accommodation actuator; and
    an antenna disposed on the substrate and electrically connected to the controller, the antenna configured to provide wireless communication with the controller and inductive charging of the battery.

11. The contact lens of claim 7, wherein the one or more pressure-sensitive sensors are disposed in the contact lens proximate to a periphery of the accommodation actuator.

12. The contact lens of claim 11, wherein the one or more pressure-sensitive sensors include an even number of pressure-sensitive sensors spaced evenly around the periphery of the accommodation actuator.

13. The contact lens of claim 11, wherein the one or more pressure-sensitive sensors include an odd number of pressure-sensitive sensors spaced evenly around the periphery of the accommodation actuator.

14. The contact lens of claim 11, wherein the one or more pressure-sensitive sensors are unevenly spaced around the periphery of the accommodation actuator.

15. A method of manual communication with an electronic contact lens, comprising:
   sensing a mechanical deformation of the electronic contact lens with a tactile sensor system disposed in the electronic contact lens, wherein the tactile sensor system including one or more pressure-sensitive sensors is disposed proximate to a periphery of the electronic contact lens, and wherein sensing the mechanical deformation includes sensing a user pressing with a finger on the one or more pressure-sensitive sensors through an eyelid of a user;
   outputting a signal from the tactile sensor system in response to the mechanical deformation of the electronic contact lens; and
   receiving the signal with a controller coupled to the tactile sensor system, wherein the controller is coupled to one or more other pieces of circuitry in the electronic contact lens; and
   adjusting an optical power of an accommodation actuator disposed in the electronic contact lens in response to the user pressing with the finger on the one or more pressure-sensitive sensors.

16. The method of claim 15, wherein a location of the mechanical deformation corresponds to a plurality of sub-signals included in the signal.

17. The method of claim 16, wherein a first sub-signal in the plurality of sub-signals is an override signal for the one or more other pieces of circuitry in the electronic contact lens.

18. The method of claim 16, wherein a second sub-signal in the plurality of sub-signals is an on/off signal.

19. The method of claim 16, wherein the user pressing on the one or more pressure-sensitive sensors includes at least one of pressing with two fingers, tapping multiple times on the electronic contact lens, tapping and holding down on the electronic contact lens, pressing in two different locations on the electronic contact lens, or a swipe across the electronic contact lens.

20. The method of claim 15, wherein the sensed mechanical deformation is determined to be an acknowledgement signal from a user in response to a low-glucose signal, a normal-glucose signal, or a high-glucose signal from the electronic contact lens.

21. The contact lens of claim 7, further comprising an accelerometer disposed in the contact lens and coupled to the controller to provide at least one of positional, rotational, directional, or acceleration feedback to the controller.

22. The contact lens of claim 7, wherein the controller further comprises logic that includes one or more preset modes, wherein the one or more preset modes include at least one of a first mode for short distance viewing, or a second mode for long distance viewing.

23. The contact lens of claim 7, wherein the controller further includes logic that when executed by the controller causes the contact lens to perform operations including:
   electrically manipulating the accommodation actuator to change the optical power of the contact lens to the one or more of the preset modes in response to a particular pressure distribution on the pressure sensitive sensors.

24. The method of claim 20, wherein the low-glucose signal, the normal-glucose signal, or the high-glucose signal includes flashing a light emitting diode disposed in the electronic contact lens.

* * * * *